United States Patent [19]
Gordziel

[11] Patent Number: 6,037,358
[45] Date of Patent: Mar. 14, 2000

[54] DECONGESTANT/ANTIHISTAMINIC COMPOSITIONS

[75] Inventor: Steven A. Gordziel, Belle Mead, N.J.

[73] Assignee: Carter-Wallace, Inc.

[21] Appl. No.: 09/275,121

[22] Filed: Mar. 24, 1999

[51] Int. Cl.⁷ .................................................. A61K 31/135
[52] U.S. Cl. ........................................... 514/357; 514/653
[58] Field of Search ....................................... 514/357, 653

[56] References Cited

U.S. PATENT DOCUMENTS 4,552,899 11/1985 Sunshine et al. ........................ 514/568
5,599,846 2/1997 Chopdekar et al. ..................... 514/653

*Primary Examiner*—Frederick Krass
*Attorney, Agent, or Firm*—Kevin B. Clarke, Esq.

[57] ABSTRACT

Tannate compositions consisting essentially of phenylephrine tannate and chlorpheniramine tannate which are effective when administered orally for the symptomatic relief of coryza associated with the common cold, sinusitis, allergic rhinitis and upper respiratory tract conditions are disclosed.

6 Claims, No Drawings

DECONGESTANT/ANTIHISTAMINIC COMPOSITIONS

FIELD OF INVENTION

The invention relates to novel decongestant/antihistaminic tannate compositions. The compositions contain as essential ingredients phenylephrine tannate and chlorpheniramine tannate.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid, the internal ester of gallic acid also frequently referred to as tannin.

Tannic Acid consists of an amorphous powder glistening scales or spongy masses varying in color from yellowish-white to light brown. Tannic acid is very soluble in water, glycerine or alcohol.

Tannic acids are usually obtained from glycosides which consist of several molecules of a tannic acid in combination with glucose.

Commercially available, tannic acid, also known as Tannin, has a complex non-uniform chemistry usually contains from about 5% to about 10% by weight water, has a molecular weight of about 1700 and is typically produced from Turkish or Chinese nutgall.

Phenylephrine, known chemically as L-m-hydroxy α [(methylamino)methyl] benzal alcohol, is a synthetic, optically active sympathomimetic amine which has one hydroxyl group on the benzene ring. The hydroxyl group is placed in the position meta to the aliphatic side chain. The meta position affords optimal activity and phenylephrine (neo-synephrine) replaced an older preparation, synephrine, in which the hydroxyl was in the para position.

Phenylephrine hydrochloride is available in the form of the levoratory isomer, a white, odorless, non-hygroscopic, crystalline compound possessing a bitter taste. Phenylephrine chloride has a melting point of 140–145° C. and is freely soluble in water and alcohol.

Chlorpheniramine, known chemically as 3-(p-chlorophenyl)-3-(2-pyridyl)-N,N-dimethylpropylamine, is a synthetic optically active d-isomer resolved from dl racemates of the amine by treating said racemate with an optically active d- or l-isomer of a substituted succinic acid in the presence of a non-reactive compatible organic solvent to cause the formation of the corresponding diasteroisomeric salts thereof, separating the salts so obtained by fractional crystallization, and releasing the desired d-isomers from the separated amine salts as more fully described in U.S. Pat. No. 3,061,517.

Chlorpheniramine maleate salt has a melting point of 130–135° C. and is slightly soluble in benzene and ether.

Decongestant and antihistamine compounds in the form of their free bases as well as their salts, e.g. hydrochloride, citrate, maleate, tannate, etc., are well known. Decongestants and antihistamines in the form of their tannate salts are very desirable because such salts are generally stable and may be combined in such form without any untoward side effects.

Decongestants and antihistaminics in the form of their tannate salts are typically prepared by reacting the free base, e.g. phenylephrine, chlorpheniramine, etc. with tannic acid in the presence of a volatile solvent, usually isopropanol.

Typically, in the conventional isopropanol route, the decongestant or antihistaminic free base and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. No. 5,599,846 and U.S. Pat. No. 5,663,415.

THE INVENTION

It has now been found that the novel combination of phenylephrine tannate and chlorpheniramine tannate produces a composition having antitussive, sympathomimetic decongestant and antihistaminic properties superior to the use of either one of the tannate compounds alone.

The compositions of the present invention may be prepared for oral administration in the form of powders, capsules, elixirs, syrups and the preferred forms of tablets or suspensions formulated so that ideally each 5 mL (approximately 1 teaspoon) of suspension would contain approximately 1.5 to 6 mg chlorpheniramine tannate and 3 to 8 mg phenylephrine tannate.

Tablets containing the unique tannate combination of the present invention are prepared in a conventional manner by the addition of suitable pharmaceutical carriers including fillers, diluents, lubricants and the like as well as conventional and well known binding and disintegrating agents. A typical tablet composition of the present invention containing starch, dibasic calcium phosphate, coloring, magnesium stearate, methylcellulose, polygalacturoic acid, povidone and talc as described in Example 1 which follows is prepared by well known conventional tabletting techniques such as those disclosed in U.S. Pat. Nos. 3,018,221; 2,798,024 and 2,757,124 and as a three-layered tablet for oral administration.

EXAMPLE 1

| Ingredient | Milligrams per Tablet |
| --- | --- |
| Chlorpheniramine Tannate | 9.0 |
| Phenylephrine Tannate | 25.0[1] |
| Starch, NF | 65.0 |
| Methylcellulose, USP | 150 |
| Polygalactouronic Acid | 32.0 |
| Dibasic Calcium Phosphate, USP, Dihydrate | 65.0 |
| Povidone, USP | 25.0 |
| Talc, USP | 5.4 |
| FD&C Red #40 Aluminum Lake-40% | 3.93 |
| D&C Blue #1 Aluminum Lake-29% | 1.0 |
| Magnesium Stearate, NF | 4.0 |
| Alcohol Specially Denatured 23A 190 Proof | 140[2] |

[1]15% excess added during manufacture
[2]Not present in finished tablet product Suspensions of the compositions of the present invention are prepared in a conventional manner such that each 5 mL (one teaspoon) contains:

| | |
| --- | --- |
| Chlorpheniramine Tannate | 4.5 mg |
| Phenylephrine Tannate | 5 mg |

The suspension formulations additionally contain benzoic acid, coloring, natural and artificial flavors, glycerin, kaolin, magnesium aluminum silicate, methyl paraben, pectin, purified water, saccharin, sodium hydroxide and sucrose or sorbitol.

Example 2, which follows, is illustrative of a typical suspension formulation of the present invention prepared by conventional well known compounding techniques.

EXAMPLE 2

| Ingredient | Milligrams per 5 mL |
|---|---|
| Chlorpheniramine Tannate | 4.5 |
| Phenylephrine Tannate | 5.0[1] |
| Pectin, USP (Medium Viscosity) | 50.0 |
| Kaolin, USP (Colloidal Powder) | 1000 |
| Magnesium Aluminum Silicate, NF | 35.0 |
| Benzoic Acid, USP | 10.0 |
| Methylparaben, NF | 2.5 |
| Sucrose, NF | 1000 |
| Saccharin Sodium, USP | 0.75 |
| Glycerin, USP | 225 |
| Flavor Black Currant Imitation | 0.91 |
| Flavor Strawberry with Other Natural Flavors | 2.28 |
| Purple Shade "R" Dye | 0.45 |
| FD&C Red #3 Dye | 0.8 |
| FD&C Yellow #5 | 0.3 |
| Sodium Hydroxide Solution-50% | 3.17[2] |
| Purified Water, USP (Deionized) adjust to | 5 ml |

[1] 15% excess added during manufacturing
[2] The quantity of Sodium Hydroxide Solution may be varied depending on the pH of the Kaolin batch For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A therapeutic composition for the symptomatic treatment of coryza associated with the common cold, sinusitis, allergic rhinitis and upper respiratory tract conditions in warm-blooded animals in need of such treatment said composition comprising pharmaceutically effective amounts of 25.0 mg phenylephrine tannate and 9.0 mg chlorpheniramine tannate.

2. A therapeutic composition as claimed in claim 1 in tablet form.

3. A therapeutic composition as claimed in claim 1 in suspension form wherein each 5 ml contains 4.5 mg chlorpheniramine tannate and 5.0 mg phenylephrine tannate.

4. A method for symptomatically treating and relieving the distress of coryza associated with the common cold, sinusitis, allergic rhinitis and upper respiratory tract conditions in warm-blooded animals which comprises orally administering to warm-blooded animals in need of such treatment the composition of claim 1.

5. A method as claimed in claim 4 wherein said composition is in tablet form.

6. A method as claimed in claim 4 wherein said composition is a suspension wherein each 5 ml contains 4.5 mg chlorpheniramine tannate and 5.0 mg phenylephrine tannate.

* * * * *